United States Patent
Wakeford et al.

(10) Patent No.: US 11,080,851 B2
(45) Date of Patent: Aug. 3, 2021

(54) METHOD, APPARATUS, AND COMPUTER-READABLE MEDIUM FOR ASSESSING QUALITY OF IMAGES PRODUCED BY SCANNING SYSTEM FOR EYE EXAMINATION

(71) Applicant: Optos PLC, Scotland (GB)

(72) Inventors: Peter Robert Wakeford, Dunfermline (GB); David Clifton, Dunfermline (GB)

(73) Assignee: OPTOS PLC, Scotland (GB)

( * ) Notice: Subject to any disclaimer, the term of this patent is extended or adjusted under 35 U.S.C. 154(b) by 111 days.

(21) Appl. No.: 16/543,063

(22) Filed: Aug. 16, 2019

(65) Prior Publication Data

US 2020/0058122 A1 Feb. 20, 2020

(30) Foreign Application Priority Data

Aug. 17, 2018 (EP) ..................................... 18189482

(51) Int. Cl.
*G06T 7/00* (2017.01)
*G06T 7/40* (2017.01)

(52) U.S. Cl.
CPC .............. *G06T 7/0012* (2013.01); *G06T 7/40* (2013.01); *G06T 2207/20021* (2013.01); *G06T 2207/30041* (2013.01); *G06T 2207/30168* (2013.01)

(58) Field of Classification Search
CPC ..................... G06T 7/0012; G06T 7/40; G06T 2207/20021; G06T 2207/30041;
(Continued)

(56) References Cited

U.S. PATENT DOCUMENTS

2009/0116713 A1* 5/2009 Yan ...................... G06K 9/4619
382/128
2012/0257164 A1 10/2012 Zee et al.
(Continued)

FOREIGN PATENT DOCUMENTS

JP  2002 222416 A  8/2002
JP  2013 005896 A  1/2013
JP  2013 166215 A  8/2013

OTHER PUBLICATIONS

R. M. Haralick et al.: "Textural Features for Image Classification," IEEE Transactions on Systems, Man, and Cybernetics, vol. SMC-3, No. 6, pp. 610-621 (Nov. 1973).
(Continued)

*Primary Examiner* — Siamak Harandi
(74) *Attorney, Agent, or Firm* — DeLucia, Mlynar & Alicandro LLP

(57) ABSTRACT

A method, apparatus, and computer-readable medium, for assessing image quality of an image produced by a scanning imaging system. The method comprises acquiring (S10) image data of an image produced by the scanning imaging system and calculating (S20 to S40), for each section of the image: a respective first value measuring at least one of sharpness or contrast of at least a part of the section, the measuring depending on noise, a respective second value measuring noise in at least a part of the section, and a respective third value indicating image quality, by combining the first and second values. The combining is such that calculated third values have a weaker dependency on the noise than the first values. The method further comprises determining (S50) a quality score that is indicative of image quality of the image based on a variation of the calculated third values among the sections.

20 Claims, 10 Drawing Sheets

(58) Field of Classification Search
CPC ......... G06T 2207/30168; G06T 7/0002; G06T 2207/10008; A61B 3/1025; A61B 3/102; A61B 3/0025
See application file for complete search history.

(56) References Cited

U.S. PATENT DOCUMENTS

| | | |
|---|---|---|
| 2014/0037222 A1* | 2/2014 | Choudhury ........... G06T 7/0004 382/235 |
| 2016/0227999 A1 | 8/2016 | An et al. |
| 2017/0039689 A1 | 2/2017 | Solanki et al. |
| 2017/0205390 A1 | 7/2017 | Shaked et al. |

OTHER PUBLICATIONS

Extended European Search Report from corresponding European Application No. 18189482.5, dated Feb. 22, 2019.
"Entropy (information theory)", Wikipedia, accessed on Nov. 28, 2019. Available at: https://en.wikipedia.org/wiki/Entropy.
"Entropy of grayscale image", MathWorks, MATLAB, United Kingdom, Accessed on Nov. 28, 2019. Available at: https://uk.mathworks.com/help/images/ref/entropy.html.
John Immerkaer, "Fast Noise Variance Estimation", Computer Vision and Image Understanding, vol. 64, No. 2, pp. 300-302 (1996). Available at: https://en.wikipedia.org/wiki/Entropy_(information_theory).
Determination of Allowance Issued in Counterpart Japanese Application No. 2019-149773 dated Feb. 2, 2021, [original Japanese version (one sheet) attached; and Machine English translation (two sheets) attached].

* cited by examiner

METHOD, APPARATUS, AND COMPUTER-READABLE MEDIUM FOR ASSESSING QUALITY OF IMAGES PRODUCED BY SCANNING SYSTEM FOR EYE EXAMINATION

This application claims priority to European Patent Application No. 18189482.5 filed Aug. 17, 2018 and is incorporated herein by reference. To the extent appropriate, a claim of priority is made to the above disclosed application.

FIELD

Example aspects here generally relate to the field of image processing and, more particularly, to the assessment of image quality of images produced by a scanning imaging system.

BACKGROUND

Scanning imaging systems are widely used in many different applications, and are generally configured to illuminate an object to be imaged by scanning a light beam (or a line of light) across the object's surface and to collect light reflected from the surface, making use of scanning elements such as galvo-mirrors, polygonal scanners, laser line scanners and the like, as well as scan transfer devices such as appropriately shaped lenses and/or mirrors, to provide a varying degree of deflection to a light beam or light line transmitted from a light source so that the light beam/line is scanned across the object's surface, and to guide light reflected from the surface to a light detector. For example, the scanning laser ophthalmoscope (SLO) is a well-known type of scanning imaging system that is commonly used to image the retina of a subject's eye.

SUMMARY

Owing to budgetary constraints, time pressure and other practicalities, the performance of scanning imaging systems is often assessed by their operators on a largely subjective basis, with the operator simply inspecting an image acquired by the scanning imaging system by eye to form a judgment on whether the quality of the image and/or set-up of the system is acceptable. This subjective approach can make it difficult to gauge the true performance of a scanning imaging system and detect a gradual degradation in its performance, for example.

In view of these limitations, the present inventor has devised a method of automatically assessing image quality of an image produced by a scanning imaging system. The method comprises acquiring image data of an image produced by the scanning imaging system and calculating, for each section of a plurality of sections of the image covering different regions of the image: a respective first value of a measure of at least one of a sharpness and a contrast of at least a part of the section, the measure being dependent on noise in the at least a part of the section; a respective second value that provides a measure of noise in at least a part of the section; and a respective third value indicative of an image quality of the section by combining the respective calculated first value with the respective calculated second value, wherein, in the calculation of the respective third value for each of the plurality of sections of the image, the respective calculated first and second values are combined in the combining such that the third values calculated for the plurality of sections have a weaker dependency on the noise than the first values calculated for the plurality of sections. The method further comprises determining a quality score that is indicative of an image quality of the image based on a variation of the calculated third values calculated among the sections.

The sharpness and/or contrast may be indicators of image quality, which are indicated by at least part of the first value. Brightness may be an indicator of image quality but is not typically measured by at least part of the first value. There may be other indicators of image quality that are indicated by at least part of the first value.

The present inventor has further devised an apparatus for assessing image quality of an image produced by a scanning imaging system. The apparatus comprises an image acquisition module arranged to acquire image data of an image produced by the scanning imaging system, and a calculation module arranged to calculate, for each a plurality of sections of the image covering different regions of the image: a respective first value of a measure of at least one of a sharpness or a contrast of at least a part of the section, the measure being dependent on noise in the at least a part of the section; a respective second value that provides a measure of noise in at least a part of the section; and a respective third value indicative of an image quality of the section by combining the respective calculated first value with the respective calculated second value. The calculation module is arranged to combine the respective calculated first and second values in the calculation of the respective third value for each of the plurality of sections of the image such that the third values calculated for the plurality of sections have a weaker dependency on the noise than the first values calculated for the plurality of sections, and determine a quality score that is indicative of an image quality of the image based on a variation of the calculated third values calculated among the sections.

The inventor has further devised a computer program comprising instructions which, when executed by a processor, cause the processor to execute the method set out above. The computer program may be stored on a non-transitory computer-readable storage device (such as a CD or a computer hard disk, for example), or it may be carried by a signal (e.g. a download over the Internet or other kind of computer network).

BRIEF DESCRIPTION OF THE DRAWINGS

Embodiments of the invention will now be explained in detail, by way of non-limiting example only, with reference to the accompanying figures, described below. Like reference numerals appearing in different ones of the figures can denote identical or functionally similar elements, unless indicated otherwise.

DETAILED DESCRIPTION OF EMBODIMENTS

Embodiments of the present invention will now be described in detail with reference to the accompanying drawings.

Figure 1:
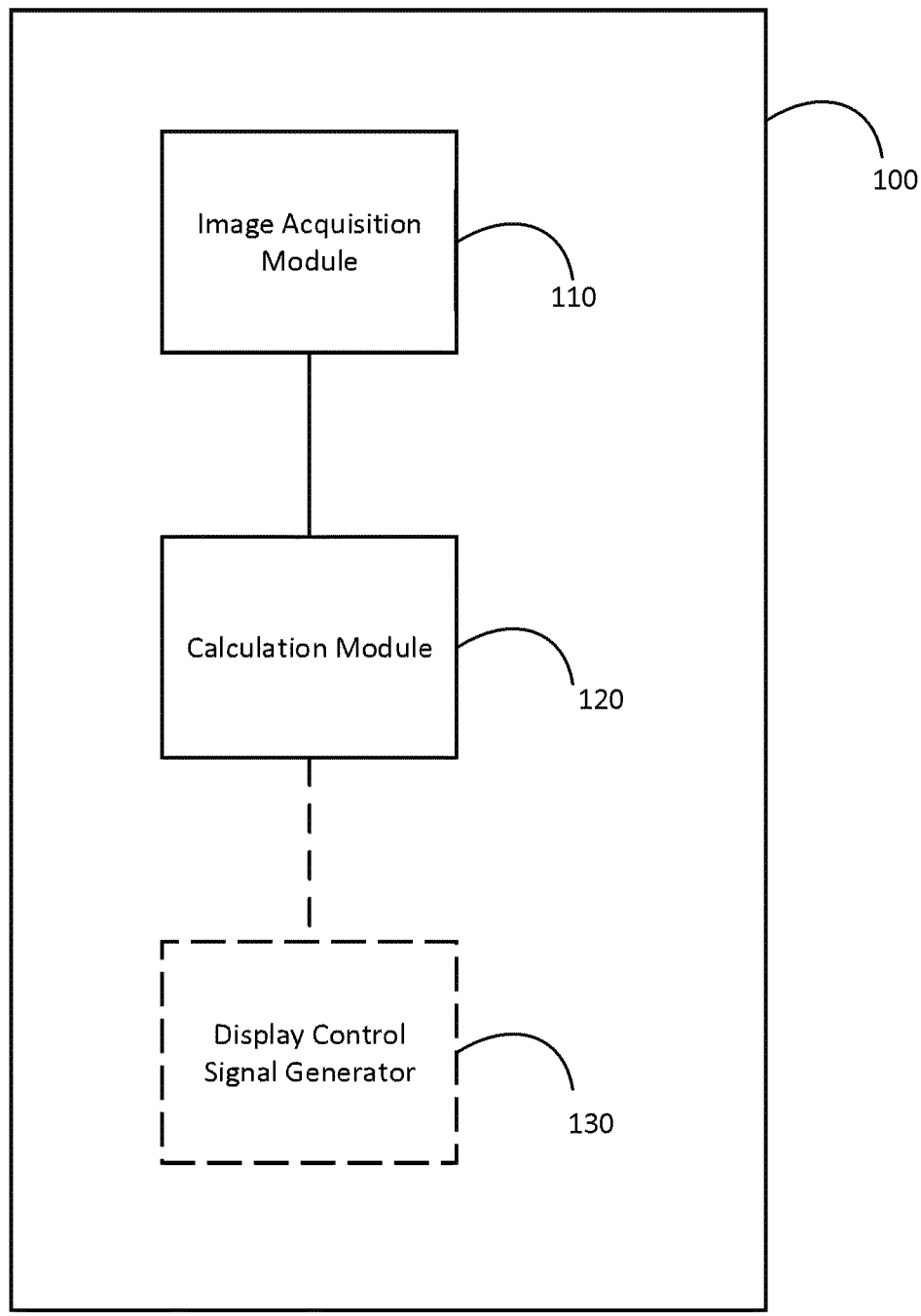
FIG. 1 is a schematic illustration of an apparatus for assessing image quality of an image produced by a scanning imaging system, according to an example embodiment herein.

FIG. 1 is a schematic illustration of an apparatus 100 for assessing image quality of an image produced by a scanning imaging system (not shown), according to an example embodiment herein. The apparatus 100 comprises an image acquisition module 110 which is arranged to acquire image data of an image produced by the scanning imaging system, and a calculation module 120 which is arranged to process the acquired image data to determine a quality score that is indicative of an image quality of the image. The apparatus 100 may, as in the present illustrated embodiment, further comprise a display control signal generator 130 (this optional component being shown by dashed lines in FIG. 1).

The scanning imaging system may be any kind of optical imaging system that is configured to deflect a light beam (or a line of light) from a light source so as to scan a projection of the light beam (or a projection of the line of light, as the case may be) across a surface or through a volume of an object being imaged, and to collect light reflected from the surface or volume during the performance of the scan to build up an image of the surface.

The scanning imaging system may, as in the example present embodiment, be a scanning laser ophthalmoscope (SLO) that is configured to acquire images of the retina of a subject's eye. By way of example, the SLO of the present embodiment is configured to capture autofluorescence (AF) images (it may be configured to capture Red-Green (RG) reflectance images or images from other fluorescence modes), although it may alternatively or additionally be configured to acquire one or more other types of images. The SLO may, for example, be an ultra-wide field SLO (UWF-SLO) capable of generating an ultra-wide field image of up to 80% of a retinal surface. Alternatively, the scanning imaging system may be another kind of retinal scanner, such as an optical coherence tomography (OCT) scanner, in which case the image processing techniques described herein are applicable to the tomographic images acquired by the OCT scanner. As a further alternative, the scanning imaging system may be a combined SLO-OCT scanner, in which case the image processing techniques described herein are applicable to both the SLO retinal scans and the OCT scans acquired by the combined SLO-OCT scanner.

The image acquisition module 110 may acquire image data of an image generated by the scanning imaging system by any suitable means known to those versed in the art. For example, the image acquisition module 110 may receive image data of the image from the scanning imaging system via a direct communication link (which may be provided by any suitable wired or wireless connection, e.g. a Universal Serial Bus (USB) or a Bluetooth™ connection), or an indirect communication link (which may be provided by a network comprising a Local Area Network (LAN), a Wide Area Network (WAN) and/or the Internet). Furthermore, the image data may be acquired by the image acquisition module 110 (and may furthermore subsequently be processed to determine a quality score, as described below) as this image data is being generated by the scanning imaging system, i.e. the image data may be acquired "on the fly", without waiting for the scanning imaging system to finish generating all of the image data that forms the image of the retina. However, in the present example embodiment, and for the purposes of this description, the image acquisition module 110 is configured to acquire all of the image data that forms the image of the retina before the calculation module 120 begins to process this data.

The calculation mode 120 is configured to perform calculations as described herein for each of a plurality of sections of the image that cover different regions of the image. For example, where the image acquisition module 110 acquires image data defining strips of the image that span opposite sides of the image, the calculation module 120 may perform these calculations for the image data of a strip once all the image data of the strip has been received and before all the image data of the next strip has been received. Alternatively, for example in embodiments like the present example embodiment, where the calculations are performed by the calculation module 120 after image data defining two or more strips (or other kinds of section) has been acquired by the image acquisition module 110, the image acquisition module 110 and/or the calculation module 120 may designate a plurality of sections of the image covering different regions of the image.

The calculation module 120 is arranged to calculate, for each of the sections: (i) a respective first value of a measure of a sharpness, a contrast, or both a sharpness and a contrast, of at least a part of the section, the measure being dependent on noise in the at least a part of the section; (ii) a respective second value that provides a measure of (random) noise in at least a part of the section; and (iii) a respective third value that is indicative of an image quality of the section, by combining the respective calculated first value with the respective calculated second value. The calculation module 120 is arranged to combine the respective calculated first and second values in the calculation of the respective third value for each of the plurality of sections of the image such that the third values calculated for the plurality of sections have a weaker dependency on the (random) noise than the first values calculated for the plurality of sections. For example, where the first values are indicative of the sharpness of at least a part of the section of the image, since the presence of random noise in the image may not significantly affect the sharpness of the image and thus the image quality as perceived by a human observer, combining the first values with the calculated second values that are indicative of the amount of noise in at least a part of the section, in the manner described above, results in third values that are less affected by the presence of noise in the section and thus provide an indication of image quality that is closer to the perceived image quality. The noise may or may not be random noise.

The calculation module 120 is further arranged to determine a quality score that is indicative of an image quality of the image based on a variation of the calculated third values among the sections, in other words the spatial distribution of the calculated third values in the image.

In embodiments like the present example embodiment, where the apparatus 100 comprises a display control signal generator 130, the display control signal generator 130 may be arranged to generate display control signals for controlling a display device (such as an LCD screen or other type of visual display unit) (not shown) to display to a user a spatial variation profile indicative of the variation of the calculated third values among the sections.

Figure 2:
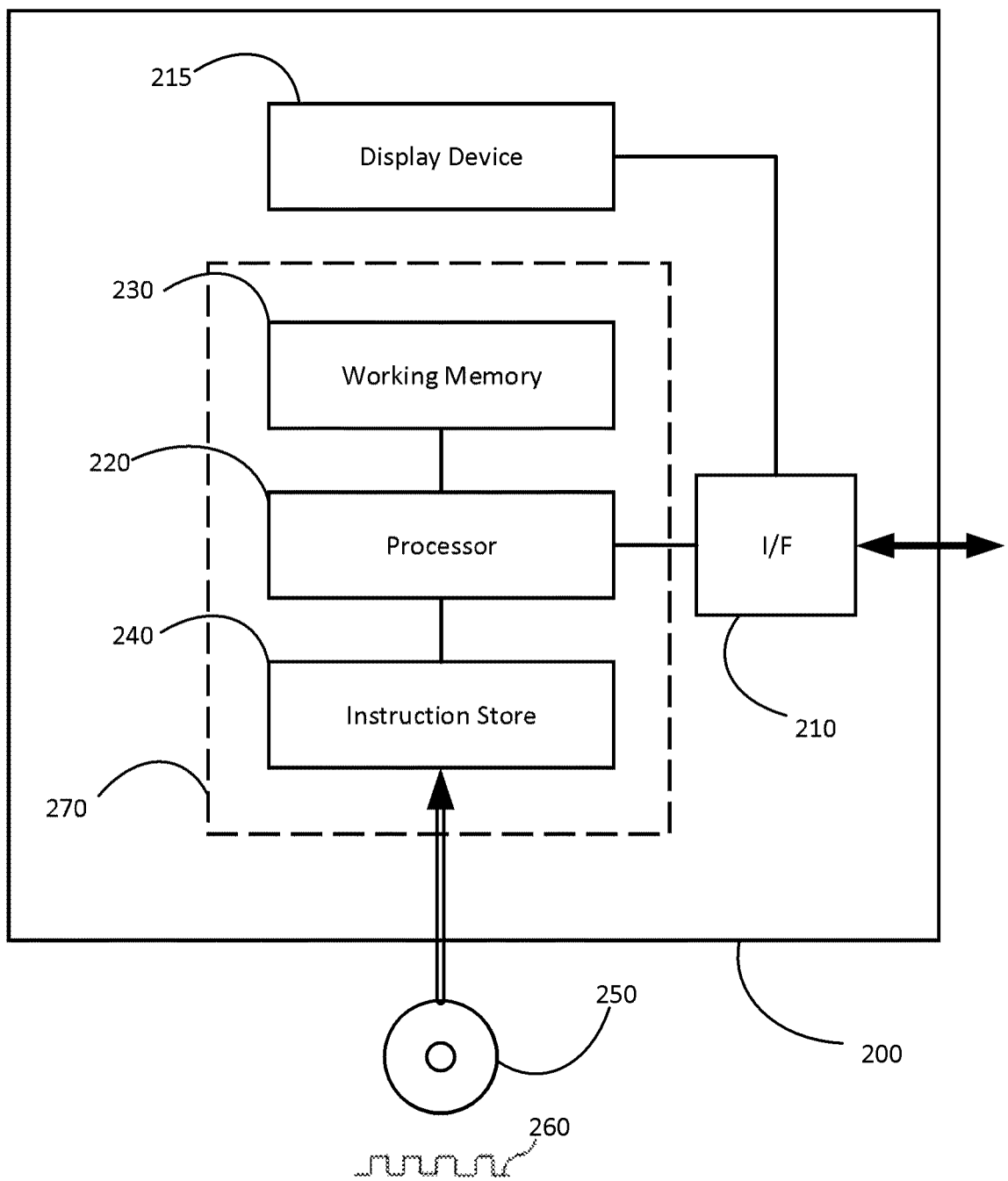
FIG. 2 is a block diagram illustrating an example of hardware configuration of the apparatus for assessing image quality, according to an example embodiment herein.

FIG. 2 shows an example of how the apparatus 100 may be implemented in programmable signal processing hardware. The signal processing apparatus 200 shown in FIG. 2 comprises a communication interface (I/F) 210 for receiving image data of an image produced by a scanning imaging system, and (optionally) outputting display control signals for controlling a display device 215 to display to a user a spatial variation profile as described below.

The signal processing apparatus 200 further comprises a processor (e.g. a Central Processing Unit, CPU, or Graphics Processing Unit, GPU) 220, a working memory 230 (e.g. a random access memory) and an instruction store 240 storing computer-readable instructions which, when executed by the processor 220, cause the processor 220 to perform the processing operations hereinafter described to assess image quality of an image produced by a scanning imaging system. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions can be input thereto from a computer program product, such as a computer-readable non-transitory storage medium 250 such as a CD-ROM, etc. or a computer-readable signal 260 carrying the computer-readable instructions. It should be noted, however, that the apparatus of the embodiments described herein may alternatively be implemented in non-programmable hardware, such as an application-specific integrated circuit (ASIC).

In the present embodiment, a combination 270 of the hardware components shown in FIG. 2, comprising the processor 220, the working memory 230 and the instruction store 240, is configured to perform functions of the image acquisition module 110 and the calculation module 120, which functions will now be described in detail below. In embodiments like the present illustrated embodiment, where the apparatus 100 comprises a control signal generator 130, the functionality of this optional component may be provided by the combination 270 of the hardware components together with the communication I/F 210.

Owing to the physical principles of operation of the scanning imaging system, images produced thereby naturally tend to have highest image quality (in terms of brightness, contrast and/or sharpness) in a portion of the image containing features of interest when the system is optimally configured to image these features, with the image quality typically being lower in the remaining part of the image. For example, in an example retinal scan obtained by a well-adjusted SLO shown in FIG. 4, image quality is highest around a central portion of the image containing the fovea of the eye and a substantial part of the retinal vasculature, with the image brightness, contrast and sharpness all decreasing towards upper and lower edges of the image. Misalignment and/or inappropriate selection of optical components in the SLO, for example, can reduce a size of the portion of the image with high image quality and/or cause a location of that portion in the image to shift in a way that reduces the visibility of at least some of the features of interest, leading to a perception of reduced image quality. The inventor has thus recognized not only a need to find a way of automatically evaluating image quality that yields results consistent with human perception of image quality, but also a need to take into account how the evaluated image quality varies across the image.

As will become more apparent from the following description of the operations performed by the apparatus 100 of the present embodiment, the apparatus 100 allows a noise-independent indicator of a sharpness and/or a contrast of parts of an image acquired by a scanning imaging system to be evaluated, in a manner, inextricably linked to computer technology, that provides performance and a result that could not be achieved by a human observer or conventional systems, wherein in the method herein both the effect of noise on the indicator values (which would cause them to deviate from the perceived image quality) and the spatial distribution of the indicator values among the parts are taken into account to yield an objective and reliable indication of how the overall quality of the image is likely to be perceived by a human observer.

The method and apparatus for assessing the quality of an image produced by a scanning imaging system that are described in more detail below may be useful in a number of applications including manufacturing quality control and trending, automated self-diagnosis to track quality over a product's lifetime, informing design changes, and assisting field service engineers.

Figure 3:
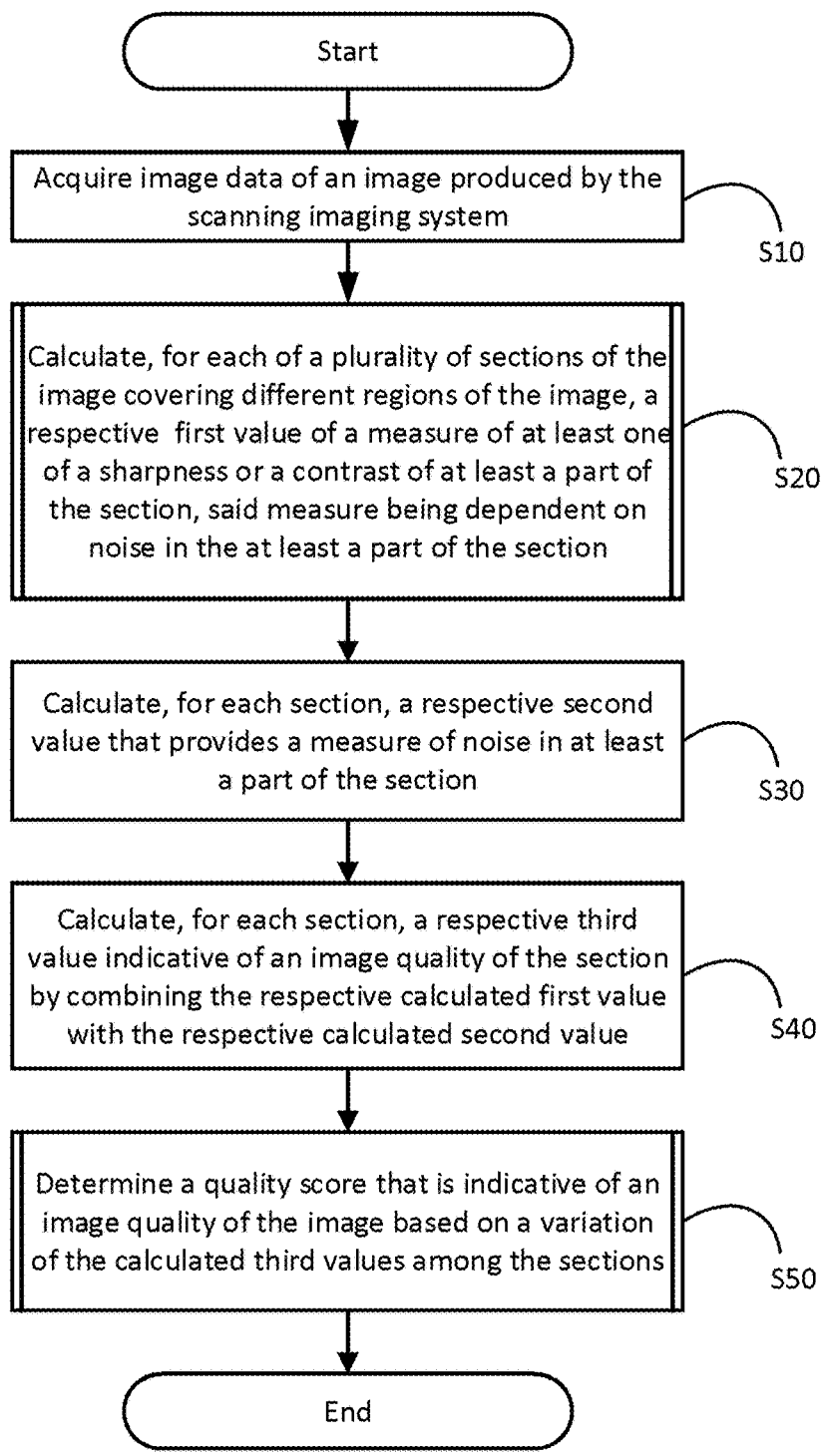
FIG. 3 is a flow diagram illustrating a process by which the apparatus assesses image quality of an image produced by a scanning imaging system, according to an example embodiment herein.

FIG. 3 is a flow diagram illustrating a process by which the apparatus 100 assesses image quality of an image produced by the scanning imaging system.

In process S10, the image acquisition module 110 acquires image data of an image produced by the SLO (as an example of a scanning imaging system), the image having been produced by the SLO scanning a part of the retina of an eye. Although the image acquisition module 110 acquires image data representing a retinal image in process S10, the acquired image data is not limited to defining a retinal image, and may alternatively define an image of a test card imaged by the scanning imaging system, for example.

Figure 4:
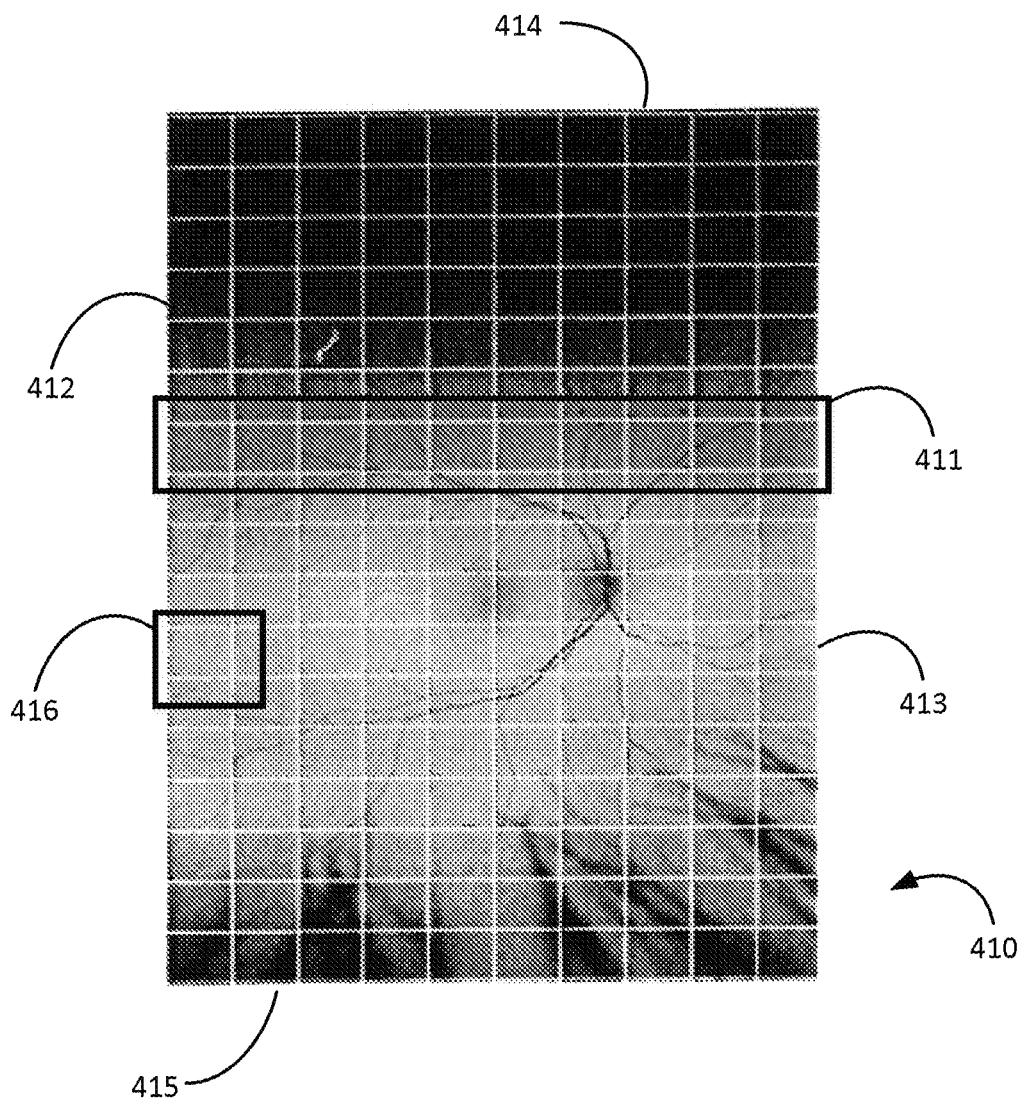
FIG. 4 is an image of a part of a retina produced by a scanning imaging system.

FIG. 4 shows an example of the acquired retinal image 410. As shown in this figure, the image 410 is brightest, sharpest and has the highest contrast in a central portion of the image, with the regions of the image 410 extending from the central portion in a vertical direction towards upper and lower edges, 414 and 415, respectively, of the image having lower brightness, sharpness and contrast. Furthermore, the image 410 shows less variation of these image qualities in a horizontal direction along the image.

As part of process S20, the calculation module 120 may, as in the present embodiment, then designate a plurality of sections of the acquired image covering different regions of the acquired image, for example, by dividing the image into non-overlapping sections, such that each section covers a different region of the acquired image.

More particularly, the calculation module 110 may, as shown in FIG. 4, designate a plurality of sections such that the regions covered by the designated plurality of sections of the acquired image form a plurality of strips 411 spanning the image 410. The strips 411 are preferably oriented with respect to the image 410 so as to maximize the variation among ("third") calculated values described below that are indicative of image quality in the strips. In the example of FIG. 4, since the greatest variation in image quality occurs along the vertical direction of the image, the strips 411 preferably are oriented to extend horizontally to span the image 410 between a left-hand side 412 of the image and a right-hand side 413 of the image 410. This horizontal arrangement of the strips provides more useful information about how the quality of the image 410 varies spatially, and thus how the scanning imaging system that produced the image is performing.

In process S20, the calculation module 120 calculates, for each section, a respective first value of a measure of sharpness and/or contrast of at least a part of the section, the measure being dependent on noise in the at least a part of the section. An example of how the calculation module 120 may perform the calculations in process S20 is illustrated in FIG. 5.

Figure 5:
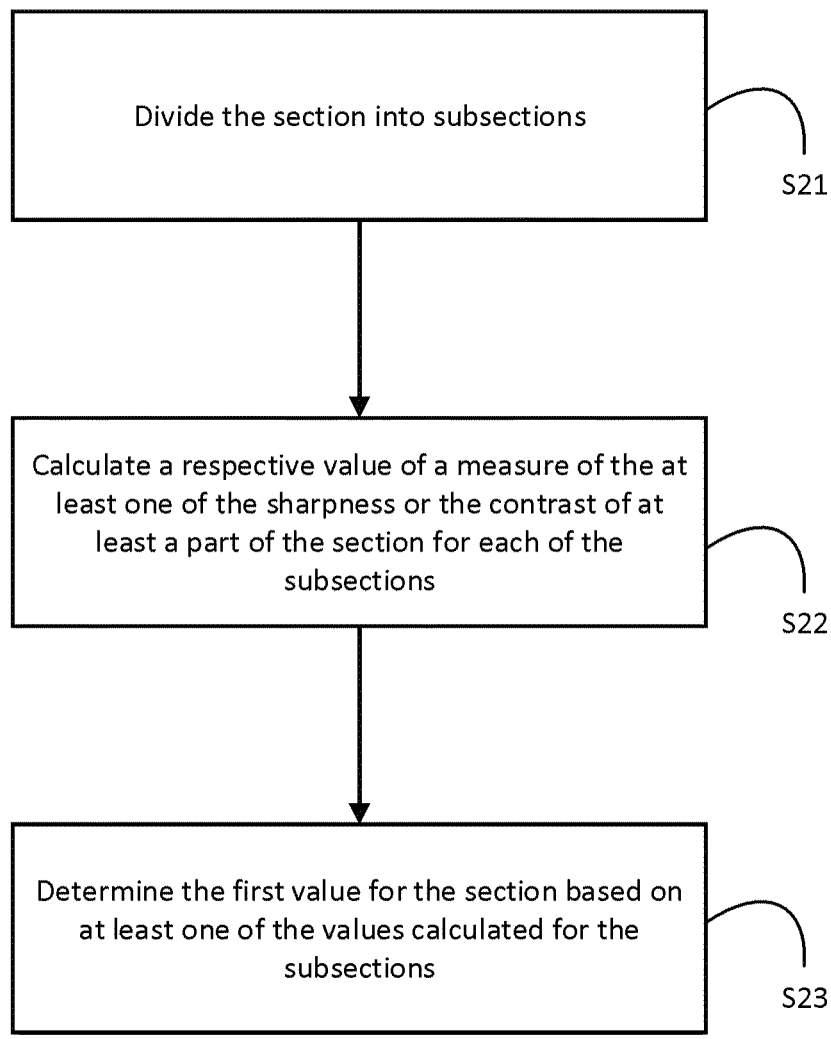
FIG. 5 is a flow diagram illustrating a process by which a calculation module 120 of the apparatus of FIG. 1 may calculate first values for each section of an image, according to an example embodiment herein.

As illustrated in FIG. 5, the calculation module 120 may calculate the first values for each section in S20 by:
(i) dividing the section into subsections (S21);
(ii) calculating a respective value that measures the sharpness and/or contrast, for each of the subsections (S22); and
(iii) determining the first value for the section based on at least one of the values calculated for the subsections in step (ii) (S23).

In the present embodiment, the first value is determined for each section in step (iii) by selecting a maximum of the values calculated (in step (ii)) for the subsections in that section. The first value for each section may alternatively be obtained by calculating the mean of the values calculated (in step (ii)) for the subsections of that section, for example. However, the former approach reduces the influence of subsections that do not contain any visible retinal features, so that a higher value of the measure would be obtained for the section as compared to a case where the first value is calculated for the section as a mean of the values calculated for the subsections.

The calculation module 120 may divide (in step (i)) each section into the subsections in any suitable way. For example, the calculation module 120 may, as in the present embodiment, divide each section into subsections by dividing each of the strips 411 shown in FIG. 4 into a plurality of blocks 416. By way of example, each strip 411 is divided lengthwise into 10 blocks 416 in FIG. 4, although the strips may more generally be divided into a greater or smaller number of blocks.

The aforementioned first values may be calculated by the calculation module 120 in one of a number of different ways. For example, in the present embodiment, the calculation module 120 calculates in step (ii) the respective value of the measure for each of the blocks 416 firstly by generating a normalized grey level co-occurrence matrix (GLCM) for each of the blocks 416 (although a GLCM for two or more of the blocks 416 may more generally be calculated).

Figure 6:
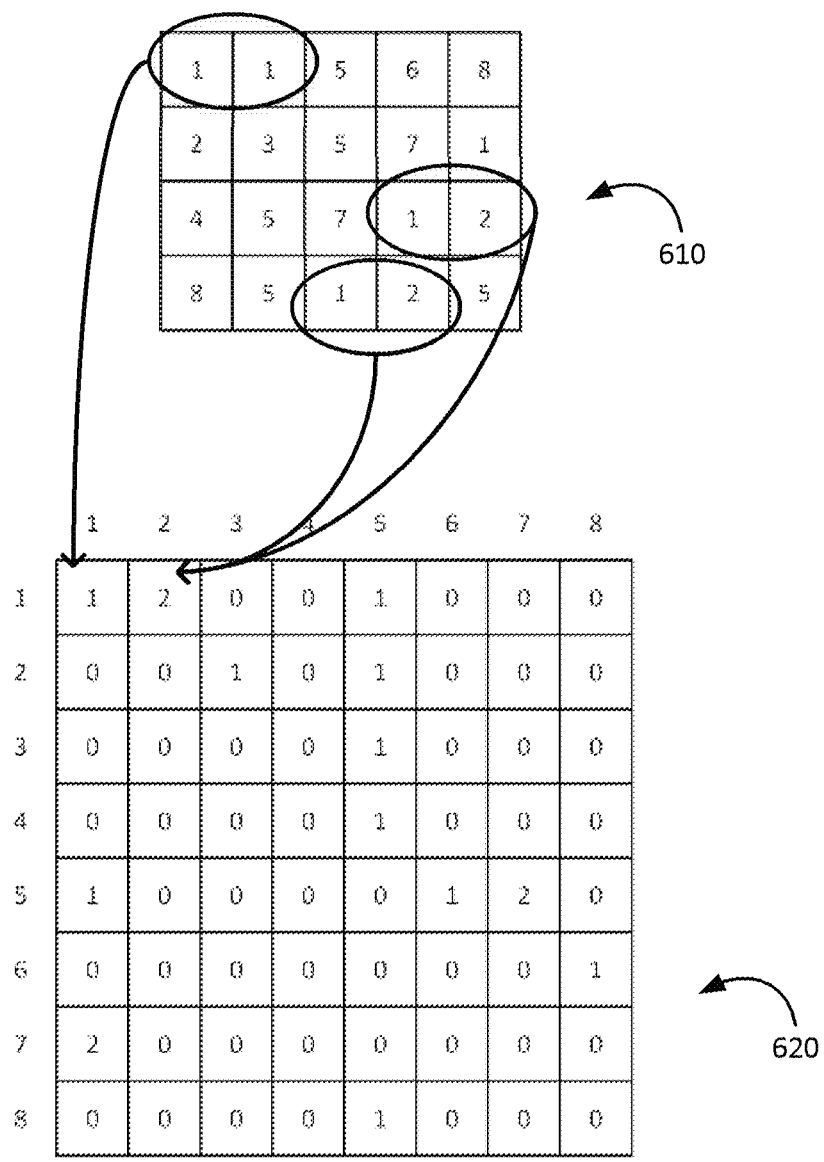
FIG. 6 is a schematic representation of a greyscale image and its associated grey level co-occurrence matrix.

For a greyscale image in which each pixel has a respective intensity, GLCM for that image indicates how often a pixel of a certain intensity occurs next to a pixel of another certain intensity. To illustrate how the GLCM may be calculated according to an example embodiment herein, reference is made to FIG. 6, which is a schematic illustration of a greyscale image 610 representing a block 416. In the present example, a GLCM 620 derived from the image 610 records how many times a pixel of a first intensity (the intensity varying from 1 to 8) occurs immediately to the right of a pixel of a second intensity, where the first intensity is shown on the horizontal axis and the second intensity is shown on the vertical axis.

As shown in GLCM 620, there is one occurrence in image 610 of a pixel of intensity 1 occurring immediately to the right of a pixel of intensity 1. In image 610, there are two occurrences of a pixel of intensity 2 occurring immediately to the right of a pixel of intensity 1, as shown in the second column of the first row of the GLCM 620. However, there are no occurrences in image 610 of a pixel of intensity 1 occurring immediately to the right of a pixel of intensity 2, as shown in the first column of the second row of the GLCM 620.

The calculation module 120 may then calculate, as the respective first value in step (iii) above, a textural feature based on a normalized form of the GLCM, where the textural feature provides a measure of at least one of a sharpness, brightness or contrast of the block 416.

An example of a textural feature having this property is the 'entropy' textural feature (as discussed in the publication entitled "Textural Features for Image Classification" by R. M. Haralick et al., IEEE Transactions on Systems, Man, and Cybernetics, Vol. SMC-3, No. 6, pages 610-621, November 1973).

It should be noted that other textural features based on the normalized GLCM may alternatively be calculated in step (iii) as a measure of the sharpness, and/or contrast of the block 416. Two examples of the measure, whose values the calculation module 120 may be configured to calculate in process S20, are the following information measures of correlation:

$$M1 = \frac{HXY - HXY1}{\max\{HX, HY\}}; \text{ and}$$

$$M2 = (1 - e^{-2(HXY2-HXY)})^{\frac{1}{2}},$$

where HXY, HXY1, HX, HY and HXY2 are defined as:

$$HXY = -\sum_{i=1}^{N_g}\sum_{j=1}^{N_g} p(i,j)\log(p(i,j))$$

$$HXY1 = -\sum_{i=1}^{N_g}\sum_{j=1}^{N_g} p(i,j)\log\{p_x(i)p_y(j)\};$$

$$HXY2 = -\sum_{i=1}^{N_g}\sum_{j=1}^{N_g} p_x(i)p_y(j)\log\{p_x(i)p_y(j)\};$$

$$HX = -\sum_{i=1}^{N_g} p_x(i)\log\{p_x(i)\}; \text{ and}$$

$$HY = -\sum_{j=1}^{N_g} p_y(j)\log\{p_y(j)\},$$

where $p(i,j)$ is the (i,j)-th matrix element of the normalized grey level co-occurrence matrix (GLCM), $N_g$ is a number of grey levels in pixels of the image, and where $p_x(i)$ and $p_y(j)$ are defined as:

$$p_x(i) = \sum_{j=1}^{N_g} p(i,j); \text{ and}$$

$$p_y(j) = \sum_{i=1}^{N_g} p(i,j).$$

By way of example, the calculation module 120, in one example embodiment herein, is arranged to calculate, as the measure of the sharpness and/or contrast of the block 416, the textural feature based on the expression $$(1 - e^{-2(HXY2-HXY)})^{\frac{1}{2}}$$

noted above.

Figure 7A:
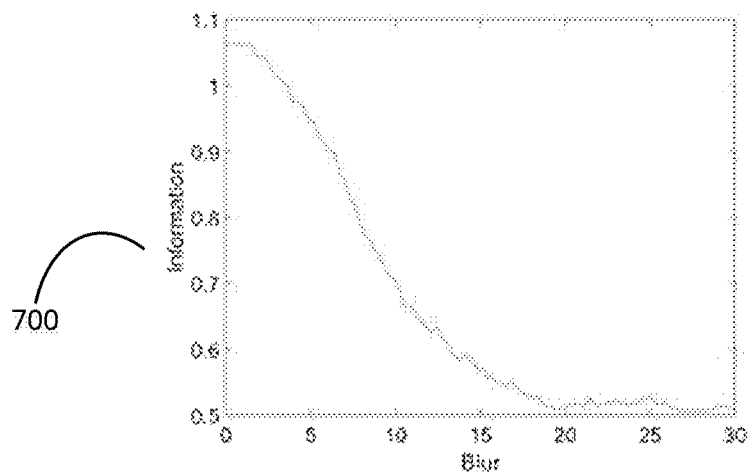
FIGS. 7(*a*) and 7(*b*) illustrate how a value of a textural feature varies with varying degree of blur in an image and varying degree of contrast of an image, respectively.
Figure 7B:
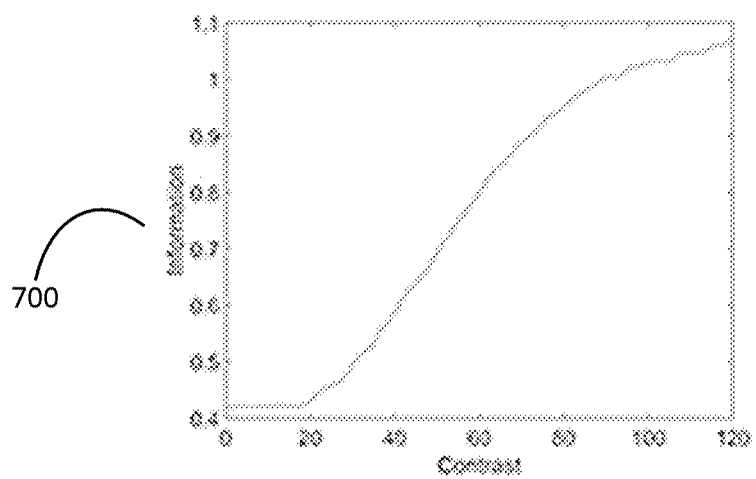

FIGS. 7(*a*) and 7(*b*) illustrate how the value of this textural feature varies with varying degree of blur in the image and varying degree of contrast of the image, respectively.

FIG. 7(*a*) shows the value of textural feature 700 (y-axis) plotted as a function of increasing blur (x-axis), i.e. decreasing sharpness. As shown in FIG. 7(*a*), the value of the textural feature decreases as the degree of blur increases (or the sharpness decreases).

FIG. 7(*b*) shows the value of the textural feature 700 (y-axis) plotted as a function of contrast (x-axis). As shown in FIG. 7(*b*), the value of the textual feature increases as contrast increases.

This textural feature therefore appears to be a good candidate for calculating an indication of how the image quality (in terms of sharpness and contrast at least) of the block 416 is likely to be perceived by an observer. However, the values of the textural feature are affected by random noise in the image, as illustrated in FIG. 7(*a*). To at least partially compensate for the dependency on noise, and referring again to the process of FIG. 3, the calculation module 120 calculates in process S30 of FIG. 3 a second value that provides a measure of an amount of noise in one or more of the blocks 416, and combines the calculated first and second values to obtain a resulting third value, such that the calculated third values are substantially independent of the noise or at least vary less with the amount of noise than the calculated first values. Further details of process S30 are provided below.

It should be noted that, according to one example embodiment, the calculation module 120 need not rely on the processing of a GLCM to calculate the respective first values of the measure of sharpness and/or contrast for the blocks 416. For example, in an alternative embodiment, the calculation module 120 may be arranged to calculate the respective first value for each subsection as an entropy of the at least a part of the subsection. Entropy is a statistical measure of randomness that can be used to characterize the texture of an input image. In order to calculate an entropy of at least a part of a subsection, a histogram of the pixel intensities P(X) in the at least a part of the subsection may be generated. For each intensity level 1 to n in the at least part of the subsection, the histogram P(X) has a respective bin. In the histogram P(X) having n bins, $x_i$ (i=1, ..., n) is the $i^{th}$ intensity level and $P(x_i)$ is a fraction of pixels in the at least part of the subsection that have an intensity or pixel value of $x_i$, that is, the fraction of pixels in the $i^{th}$ bin of the histogram, and where $x_1$ to $x_n$ are n quantization levels into which the pixel values of the image data are quantised. An entropy of at least part of the subsection may be defined as:

$$-\sum_{i=1}^{n} P(x_i)\log_2\{P(x_i)\}.$$

Process S30 will now be described in more detail. In process S30, the calculation module 120 calculates, for each image section, a respective second value that provides a measure of noise in at least a part of the section. For example, the calculation module 120 may be arranged to calculate each of the second values by applying Immerkaer's method to at least a portion or part of the strip 411 (for example, one or more of the blocks 416) or, as in the present embodiment, to the whole strip 411, wherein the strip 411 may form a whole or part of the section.

Immerkaer's method may be particularly suitable for the purpose of calculating a respective second value for use in assessing image quality of an image produced by a scanning imaging system because it can be used to give a local estimate of noise variance in a case in which the noise variance varies across the image.

Noise is typically estimated using Immerkaer's method using the following equation:

$$\text{noise} = 0.79 \frac{\pi}{12HW} \sum_{\text{image region or stip}} I * K$$

where H and W are the height and width of the image I respectively, and * denotes convolution of two arrays, in this case of image I with kernel K.

$$K = \begin{bmatrix} 1 & -2 & 1 \\ -2 & 4 & -2 \\ 1 & -2 & 1 \end{bmatrix}$$

The calculation module 120 may alternatively be arranged to calculate each of the second values by calculating a statistical measure of noise in the at least a part of the section that is indicative of a variance of pixel values in the at least a part of the section. As a further alternative, the calculation module 120 may be arranged to calculate each of the second values by generating a normalized GLCM for the at least a part of the section and calculating, as the second value, a variance measure based on the normalized GLCM, wherein the variance measure is calculated using one of:

$$f_4 = \sum_{i=1}^{N_g} \sum_{j=1}^{N_g} (i-\mu)^2 p(i,j);$$

$$f_7 = \sum_{i=2}^{2N_g} (i-f_8)^2 p_{x+y}(i); \text{ and}$$

$$f_{10} = \text{variance of } p_{x-y}.$$

wherein p(i,j) is the (i,j)-th matrix element in the normalized GLCM, $N_g$ is a number of grey levels in pixels of the image, μ is a mean of p(i,j), and $p_{x+y}$, $p_{x-y}$ and $f_8$ are defined as:

$$p_{x+y}(k) = \sum_{\substack{i=1 \\ i+j=k}}^{N_g} \sum_{j=1}^{N_g} p(i,j), k = 2, 3, \ldots, 2N_g;$$

$$p_{x-y}(k) = \sum_{\substack{i=1 \\ |i-j|=k}}^{N_g} \sum_{j=1}^{N_g} p(i,j), k = 0, 1, \ldots, N_g - 1; \text{ and}$$

$$f_8 = -\sum_{i=2}^{2N_g} p_{x+y}(i)\log\{p_{x+y}(i)\}.$$

In the present embodiment, in which the calculation module 120 is arranged to generate a normalized GLCM for use in calculating each of the second values, the GLCM may be generated as described above in relation to the calculation of the first values.

In process S40 of FIG. 3, the calculation module 120 calculates, for each strip 411, a respective third value indicative of an image quality of the section containing strip 411 by combining the calculated first value with the calculated second value. The calculation module 130 combines the calculated first and second values such that the calculated third values have a weaker dependency on the noise than the calculated first values.

As an example, the calculation module 120 may, as in the present embodiment, calculate the respective third value for each section by dividing the calculated first value by the calculated second value. The calculation module 120 may alternatively calculate the respective third value for each section by dividing the calculated second value by the calculated first value.

In process S50 of FIG. 3, the calculation module 130 determines a quality score that is indicative of an image quality of the image 410 based on a variation of the calculated third values among the strips 411.

Figure 8:
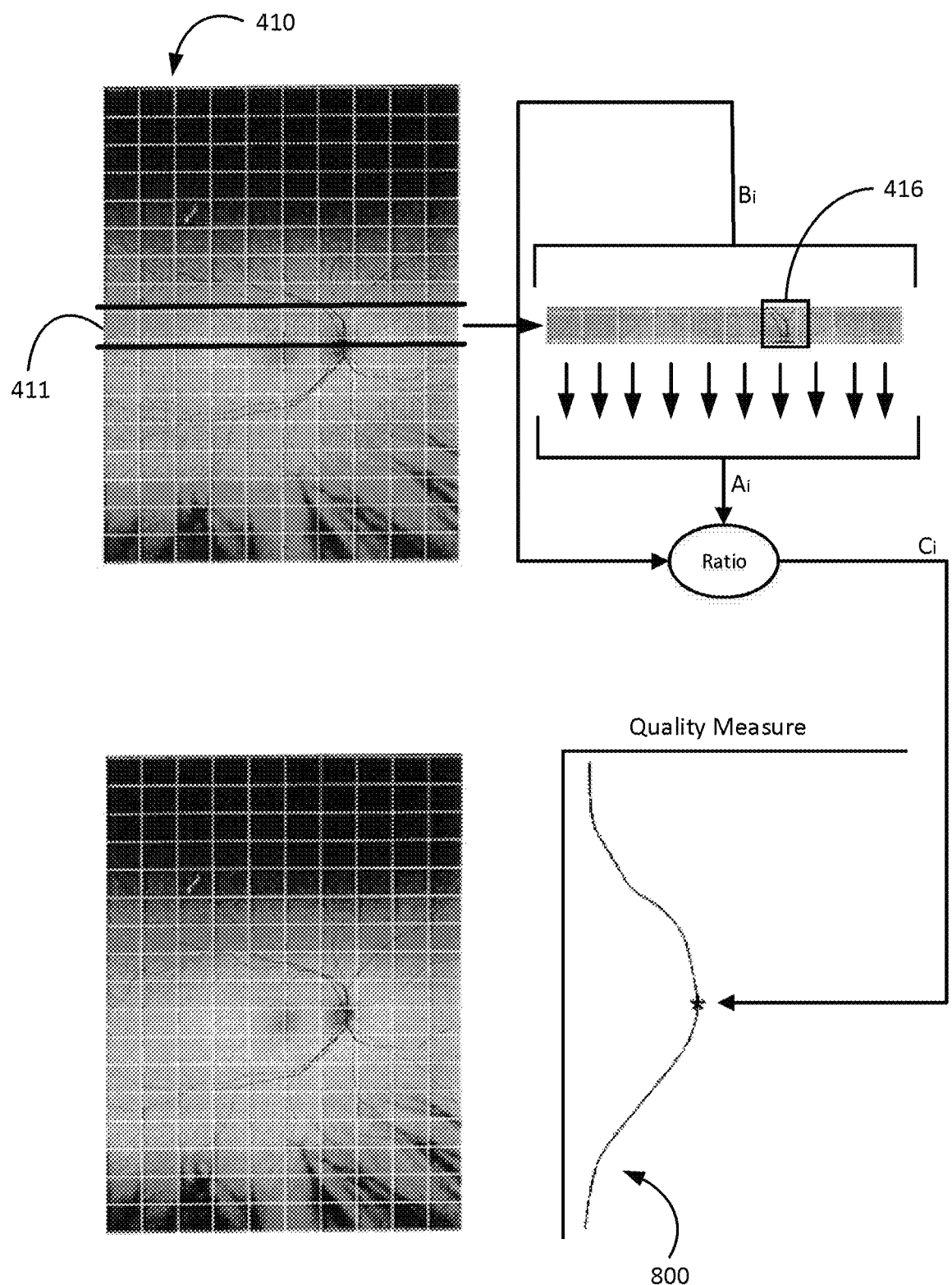
FIG. 8 is a schematic representation showing how a quality score may be determined, according to an example aspect herein.

The calculated third values may, as in the present embodiment, vary among the strips with a distribution having a peak, as shown in FIG. 8.

More particularly, FIG. 8 is a schematic showing a representation of how at least part of the procedure of FIG. 3 is performed by calculation module 120 to calculate the quality score, according to one example embodiment herein. The calculation module 120 calculates the first value discussed above for the i-th strip 411 by taking a maximum value A among the first values calculated for the blocks 416 (in step S20), applies Immerkaer's method to the image data of the whole of the i-th strip 411 to calculate the second value discussed above (labelled $B_i$ in FIG. 8) (step S30), calculating $C_i = A_i/B_i$ as the third value that is indicative of the image quality of the strip 411 (step S40), repeats these calculations for all of the strips 411 to generate a spatial variation profile 800 showing how the calculated third values vary among the strips 411 and thus spatially across the image 410, and determines (in step S50) a quality score that is indicative of the overall image quality of the image based on the spatial variation profile 800. As illustrated in FIG. 8, the calculated third values vary among the sections 411 with a distribution having a peak.

The calculation module 120 may, as in the present embodiment, be arranged to determine the quality score by determining at least one of a value of the peak, a flatness of the spatial variation profile 800, a width of the spatial variation profile 800 and rate of fall-off of the spatial variation profile 800.

The third value $C_i$ may be calculated by the ratio of $A_i/B_i$. In an alternative embodiment, powers (e, f) can used to balance the two terms, such as $C_i = A_i^e/B_i^f$.

Figure 9:
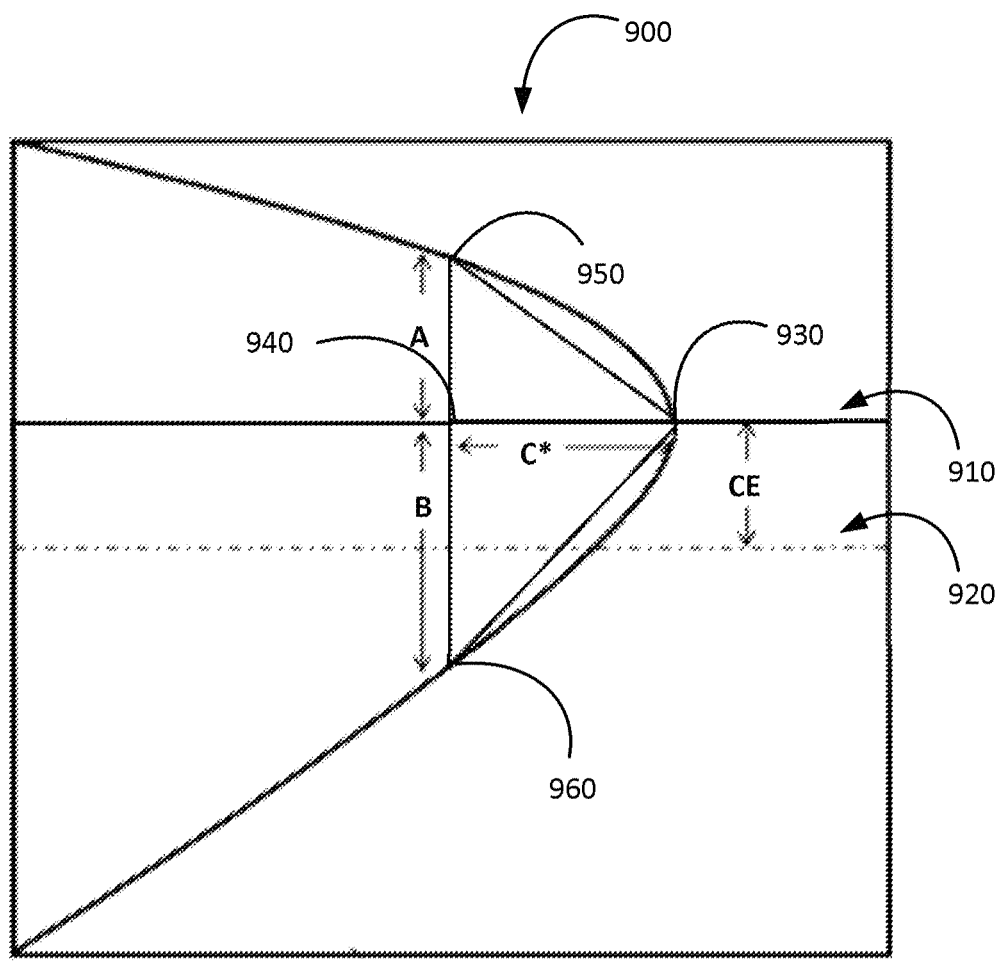
FIG. 9 is a schematic illustration of an example spatial variation profile obtained by the calculation module 120 of the apparatus of FIG. 1, according to an example embodiment herein.

FIG. 9 shows a spatial variation profile 900 of the parameter of interest, which is based on the calculated third value (and may, as in the present embodiment, simply be the third value, or more generally be indicative of the third value). Spatial variation profile 900 may be generated as described above with reference to FIG. 8.

The spatial variation profile 900 has a peak centre line 910 and an image centre line 920. Height CE represents the offset between the peak centre line 910 and an image centre line 920.

In an ideal image produced by a scanning imaging system, optimal peak of the spatial distribution of the parameter could, for example, occur at the centre of the image. As discussed above, misalignment of components of the scanning imaging system may result in an offset from the centre of the image of the portion of the image having highest quality. Offset CE may be compared to a certain threshold. If offset CE exceeds the threshold because the brightness peak centre line 910 is significantly offset from the image centre line 920, the quality score may be set equal to zero. Alternatively, a warning may be displayed to the operator.

If the quality score is outside an accepted range, this may indicate that the scanning imaging system is configured incorrectly. Accordingly, offset CE may be used as a metric to assess system performance of the scanning imaging system.

Distance C* indicates a difference between the peak value 930 of the profile and a value that is a 30% attenuation of the peak value of the profile. Distances A and B are distances from a point 940 on the parameter of interest peak centre line 910 that is a 30% attenuation of the peak value to a point (950, 960) on the profile directly above or below this point. Distances A and B represent the extent above and below the parameter of interest peak centre line 910, respectively, for which the brightness of the sections is 30% attenuation or less of the peak value. Accordingly, distances A, B and C* may be used to determine the flatness, width and rate of fall-off of the spatial variation profile.

In particular, flatness of the spatial variation profile may be defined as 1/C*. The width of the spatial variation profile may be defined as A+B, and the rate of fall-off of the profile may be defined as C/A for the portion of the image above the parameter of interest peak centre line 910, and as C/B for the portion of the image below the parameter of interest peak centre line 910.

In a satisfactory image produced by a scanning imaging system, the parameter of interest should remain sufficiently high across at least a portion of the image containing features of interest so that these features are clearly discernible. Accordingly, where the rate of fall-off of the spatial variation profile 900 is high, this provides an indication that there is a significant loss of image quality towards the upper and lower edges of the image. Therefore, a rate of fall-off exceeding a predetermined value may be indicative that the scanning imaging system is not performing correctly.

Furthermore, in cases where the spatial variation profile 900 is very flat, this is indicative of a image quality remaining relatively constant towards the upper and lower edges of the image. Therefore, where a value of flatness of the spatial variation profile 900, for example 1/C* as in the present embodiment, is less than a predetermined value, this may be indicative that the scanning imaging system is not performing correctly.

Where the spatial variation profile 900 is very wide, this is indicative of the parameter of the image quality remaining relatively constant towards the upper and lower edges of the image. Therefore, where the width of the profile 900 is less than a predetermined value, this may be indicative that the scanning imaging system is not performing correctly.

Once the spatial variation profile that is indicative of the variation of the calculated third values among the sections has been calculated, the display control signal generator 130 (if included in the apparatus 100) may generate display control signals for controlling the display device to display the spatial variation profile.

The procedures performed by the calculation module 120 can be performed on any quality profile. It can be used for one or more of the first, second or third values, or indeed the brightness profile of the image where the brightness may be calculated by integrating the image over rows or columns.

Modifications

Many modifications may be made to the embodiments described above, which would be encompassed by the claims.

The order in which some of the processes are performed by the components of the apparatus 100 for assessing image quality may be varied. For example, the order in which processes S20 and S30 in FIG. 3 are performed may be reversed. Furthermore, although the calculation module 120 may, as in the present embodiment, first calculate a first value for each of the sections, then calculate a second value for each of the sections and then calculate a third value for each of the sections, the calculation module 120 may alternatively calculate a respective first value, a respective second value and a respective third value for each section, before the calculating first, second and third values for the next section.

Furthermore, in the above embodiments, the image acquisition module 110 or the calculation module 120 designates a plurality of sections such that the regions covered by the designated plurality of sections of the acquired image form a plurality of strips 411 spanning the image 410. However, the sections may be designated in any other suitable way. For example, in an alternative embodiment, the image acquisition module 110 or the calculation module 120 may designate a plurality of sections such that the regions covered by the designated sections of the acquired image form a two-dimensional array of blocks. Such blocks may be similar to block 416 as shown in FIG. 4. In such variants, the calculation module 120 may be arranged to determine the quality score based on a spatial variation of the third values among the two-dimensional array of blocks.

In an alternative embodiment the profile can be analyzed along vertical rather than horizontal strips. This may be along either the x or y axis.

In the above embodiment, the image acquisition module 110 or the calculation module 120 designates the sections by dividing the image into non-overlapping sections, each of which covers a different region of the acquired image. The image acquisition module 110 or the calculation module 120 may alternatively designate the sections such that each of the sections covers a different region of the acquired image, and the regions covered by the sections have some (preferably small) degree of overlap. The respective regions covered by the designated sections may overlap in one or more directions.

By way of further example, in the above embodiments, the calculation module 120 divides the section into subsections by dividing each strip 411 into non-overlapping blocks 416. However, in an alternative embodiment, the blocks may have some degree of overlap. Furthermore, the calculation module 120 may divide the section 411 into subsections by dividing each of the strips 411 into further (sub-)strips that extend along the same directions as the strips 411.

In the above embodiments, the GLCM records how many times a first pixel of a certain intensity occurs immediately to the right of a second pixel of another certain intensity in the block 416. However, in other embodiments, the GLCM may be calculated using any another suitable kind of spatial arrangement between the first and second pixels, for example where the second pixel is to the left, above, below or disposed diagonally to the first pixel, with the second pixel not necessarily being adjacent to the first pixel.

Figure 10:
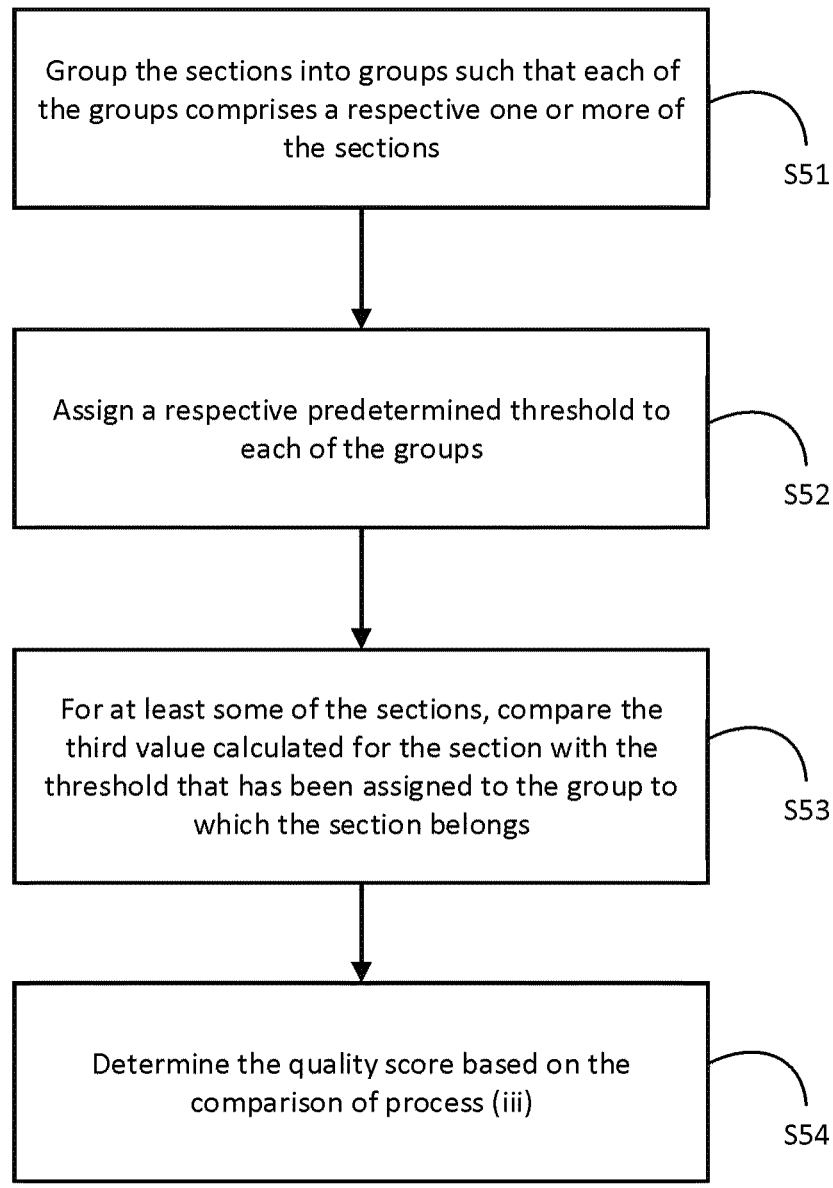
FIG. 10 is a flow diagram illustrating an example process by which the calculation module 120 of the apparatus of FIG. 1 may determine a quality score, according to another example embodiment herein.

In the above embodiments, the calculated third values vary among the sections with a distribution having a peak, and the calculation module 120 is arranged to determine the quality score by determining (in step S50 of FIG. 3) at least one of a value of the peak, a flatness of the distribution, a width of the distribution and rate of fall-off of the distribution. In an alternative embodiment, step S50 may alternatively include the steps represented in FIG. 10, wherein the calculation module 120 is arranged to determine the quality score by processes of:

(i) grouping the sections into groups such that each of the groups comprises a respective one or more of the sections (S51);

(ii) assigning a respective predetermined threshold to each of the groups (S52);

(iii) for at least some of the sections, comparing the third value calculated for the section with the predetermined threshold that has been assigned to the group to which the section belongs (S53); and (iv) determining the quality score based on the comparison in process (iii) (S54).

In this variant, the groups of sections and the respective threshold for each group may be chosen so as to best reflect the expected variation of the third values in an ideal image among the sections. Alternatively, in another embodiment, the calculation module 120 may be arranged to determine the quality score based on comparisons of at least some of the calculated third values with respective predetermined thresholds.

By way of further alternative, in another embodiment, the calculation module 120 may be arranged to determine the quality score based on comparisons of at least some of the calculated third values with a single predetermined threshold.

In summary, the following embodiments E1 to E13 of the apparatus 100 have been disclosed:

E1. An apparatus (100) for assessing image quality of an image produced by a scanning imaging system, the apparatus comprising:
  an image acquisition module (110) arranged to acquire (S10) image data of an image produced by the scanning imaging system; and
  a calculation module (120) arranged to calculate, for each of a plurality of sections (411) of the image covering different regions of the image:
    a respective first value of a measure of at least one of a sharpness or a contrast of at least a part of the section (411), the measure being dependent on noise in the at least a part of the section;
    a respective second value that provides a measure of noise in at least a part of the section (411); and
    a respective third value indicative of an image quality of the section by combining the respective calculated first value with the respective calculated second value,
  wherein the calculation module (120) is arranged to combine the respective calculated first and second values in the calculation of the respective third value for each of the plurality of sections (411) of the image such that the third values calculated for the plurality of sections (411) have a weaker dependency on the noise than the first values calculated for the plurality of sections (411), and and wherein the calculation module (120) is arranged to determine a quality score that is indicative of an image quality of the image based on a variation of the calculated third values among the sections (411).

E2. The apparatus of embodiment E1, wherein the calculation module (120) is arranged to calculate each of the second values by at least one of processing the at least a part of the section (411) using Immerkaer's method, calculating a statistical measure of noise in the at least a part of the section (411), and generating a normalized grey level co-occurrence matrix, GLCM, for the at least a part of the section (411) and calculating, as the second value, a variance measure based on the normalized GLCM, wherein the variance measure is calculated using any one of:

$$f_4 = \sum_{i=1}^{N_g} \sum_{j=1}^{N_g} (i-\mu)^2 p(i, j);$$

$$f_7 = \sum_{i=2}^{2N_g} (i-f_8)^2 p_{x+y}(i); \text{ and}$$

$$f_{10} = \text{variance of } p_{x-y},$$

wherein p(i,j) is an (i,j)th matrix element in the normalized GLCM, $N_g$ is a number of grey levels in pixels of the image, $\mu$ is a mean of p(i,j), and $p_{x+y}$, $p_{x-y}$ and $f_8$ are defined, respectively, as:

$$p_{x+y}(k) = \sum_{\substack{i=1 \\ i+j=k}}^{N_g} \sum_{j=1}^{N_g} p(i, j), k = 2, 3, \ldots, 2N_g;$$

$$p_{x-y}(k) = \sum_{\substack{i=1 \\ |i-j|=k}}^{N_g} \sum_{j=1}^{N_g} p(i, j), k = 0, 1, \ldots, N_g - 1; \text{ and}$$

$$f_8 = -\sum_{i=2}^{2N_g} p_{x+y}(i)\log\{p_{x+y}(i)\}.$$

E3. The apparatus of embodiment E1 or E2, wherein the calculation module (120) is arranged to calculate the respective first value for each section (411) using the following expression which defines an entropy of the at least a part of the section:

$$-\sum_{i=1}^{n} P(x_i)\log_2\{P(x_i)\},$$

wherein $P(x_i)$ denotes a fraction of pixels in the at least part of a subsection that have a pixel value of $x_i$, where $x_1$ to $x_n$ are n quantization levels into which pixel values of the image data are quantised.

E4. The apparatus of embodiment E1 or E2, wherein the calculation module (120) is arranged to calculate the respective first value of the measure of the at least one of the sharpness and the contrast of at least a part of the section (411) for each section (411) by:

generating a normalized grey level co-occurrence matrix, GLCM, for the at least a part of the section (411); and calculating, as the first value, a textural feature based on the normalized GLCM, wherein the textural feature is calculated using any one of the following:

$$M1 = \frac{HXY - HXY1}{\max\{HX, HY\}}; \text{ and}$$

$$M2 = (1 - e^{-2(HXY2-HXY)})^{\frac{1}{2}},$$

wherein HXY, HXY1, HX, HY and HXY2 are defined as:

$$HXY = -\sum_{i=1}^{N_g} \sum_{j=1}^{N_g} p(i, j)\log(p(i, j));$$

$$HXY1 = -\sum_{i=1}^{N_g} \sum_{j=1}^{N_g} p(i, j)\log\{p_x(i)p_y(j)\};$$

$$HXY2 = -\sum_{i=1}^{N_g} \sum_{j=1}^{N_g} p_x(i)p_y(j)\log\{p_x(i)p_y(j)\};$$

$$HX = -\sum_{i=1}^{N_g} p_x(i)\log\{p_x(i)\}; \text{ and}$$

$$HY = -\sum_{j=1}^{N_g} p_y(j)\log\{p_y(j)\},$$

wherein p(i,j) is the (i,j)-th matrix element of the normalized GLCM, $N_g$ is a number of grey levels in pixels of the image, and wherein $p_x(i)$ and $p_y(j)$ are defined as:

$$p_x(i) = \sum_{j=1}^{N_g} p(i, j); \text{ and}$$

$$p_y(j) = \sum_{i=1}^{N_g} p(i, j).$$

E5. The apparatus of any of embodiments E1 to E4, wherein the calculation module (120) is arranged to calculate the first values for each section (411) by:

dividing (S21) the section into subsections (416);

calculating (S22) a respective value of a measure of the at least one of the sharpness or the contrast of at least a part of the section (411) for each of the subsections (416); and determining (S23) the first value for the section (411) based on at least one of the values calculated for the subsections (416).

E6. The apparatus of embodiment E5, wherein the calculation module (120) is arranged to calculate the first value for the section (411) as a mean of the values calculated for the subsections (416) or a maximum of the values calculated for the subsections (416).

E7. The apparatus of any of embodiments E1 to E6, wherein the calculation module (120) is arranged to calculate the respective third value for each section (411) by dividing one of the calculated first value and the calculated second value by the other of the calculated first value and the calculated second value.

E8. The apparatus any of embodiments E1 to E7, wherein the calculation module (120) is arranged to determine the quality score based on comparisons of at least some of the calculated third values with respective predetermined thresholds.

E9. The apparatus of embodiment E8, wherein the calculation module (120) is arranged to determine the quality score by processes of:
   (i) grouping (S51) the sections into groups such that each of the groups comprises a respective one or more of the sections (411);
   (ii) assigning (S52) a respective predetermined threshold to each of the groups;
   (iii) for at least some of the sections, comparing (S53) the third value calculated for the section (411) with the predetermined threshold that has been assigned to the group to which the section belongs; and
   (iv) determining (S54) the quality score based on the comparison in process (iii).

E10. The apparatus of any of embodiments E1 to E7, wherein the calculated third values vary among the sections (411) with a distribution having a peak, and the calculation module (120) is arranged to determine the quality score by determining at least one of a value of the peak, a flatness of the distribution, a width of the distribution and rate of fall-off of the distribution.

E11. The apparatus of any of embodiments E1 to E10, wherein the regions covered by the plurality of sections of the acquired image form one of an array of strips (411) or a two-dimensional array of blocks (416).

E12. The apparatus of any of embodiments E1 to E11, further comprising:
   a display control signal generator (130) arranged to generate display control signals for controlling a display device to display a spatial variation profile indicative of a variation of the calculated third values among the sections.

E13. The apparatus of any of embodiments E1 to E12, wherein the image is a scan of one of a test card and a part of a retina of an eye, acquired by the scanning imaging system.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

The invention claimed is:

1. A method of assessing image quality of an image produced by a scanning imaging system, the method comprising:
   acquiring image data of an image produced by the scanning imaging system;
   calculating, for each section of a plurality of sections of the image covering different regions of the image
      a respective first value of a measure of at least one of a sharpness or a contrast of at least a part of the section, the measure being dependent on noise in the at least a part of the section,
      a respective second value that provides a measure of noise in at least a part of the section, and
      a respective third value indicative of an image quality of the section by combining the respective calculated first value with the respective calculated second value,
   wherein, in the calculation of the respective third value for each of the plurality of sections of the image, the respective calculated first value and the respective calculated second value are combined in the combining such that the third values calculated for respective sections of the plurality of sections have a weaker dependency on the noise than the first values calculated for respective sections of the plurality of sections; and
   determining a quality score that is indicative of an image quality of the image based on a variation of the calculated third values among the sections.

2. The method of claim 1, wherein each of the second values is calculated by at least one of
   processing the at least a part of the section using Immerkaer's method,
   calculating a statistical measure of noise in the at least a part of the section, and
   generating a normalized grey level co-occurrence matrix, GLCM, for the at least a part of the section and calculating, as the second value, a variance measure based on the normalized GLCM, wherein the variance measure is calculated using any one of:

$$f_4 = \sum_{i=1}^{N_g}\sum_{j=1}^{N_g}(i-\mu)^2 p(i,j);$$

$$f_7 = \sum_{i=2}^{2N_g}(i-f_8)^2 p_{x+y}(i); \text{ and}$$

$$f_{10} = \text{variance of } p_{x-y},$$

wherein $p(i,j)$ is an $(i,j)$-th matrix element in the normalized GLCM, $N_g$ is a number of grey levels in pixels of the image, $\mu$ is a mean of $p(i,j)$, and $p_{x+y}$, $p_{x-y}$ and $f_8$ are defined, respectively, as:

$$p_{x+y}(k) = \sum_{\substack{i=1\\i+j=k}}^{N_g}\sum_{j=1}^{N_g} p(i,j), k=2,3,\ldots,2N_g;$$

$$p_{x-y}(k) = \sum_{\substack{i=1\\|i-j|=k}}^{N_g}\sum_{j=1}^{N_g} p(i,j), k=0,1,\ldots,N_g-1; \text{ and}$$

$$f_8 = -\sum_{i=1}^{2N_g} p_{x+y}(i)\log\{p_{x+y}(i)\}.$$

3. The method of claim 1, wherein the respective first value is calculated for each section using an expression which defines an entropy of the at least a part of the section, wherein the expression is:

$$-\sum_{i=1}^{n} P(x_i)\log_2\{P(x_i)\}$$

and wherein $P(x_i)$ denotes a fraction of pixels in the at least part of a section that has a pixel value of $x_i$, where $x_1$ to $x_n$ are n quantization levels into which pixel values of the image data are quantised.

4. The method of claim 1, wherein the respective first value of the measure of the at least one of the sharpness or the contrast of at least a part of the section is calculated for each section by:
   generating a normalized grey level co-occurrence matrix, GLCM, for the at least a part of the section; and
   calculating, as the first value, a textural feature based on the normalized GLCM, wherein the textural feature is calculated using any one of the following:

$$M1 = \frac{HXY - HXY1}{\max\{HX, HY\}}; \text{ and}$$

$$M2 = (1 - e^{-2(HXY2-HXY)})^{\frac{1}{2}}$$

wherein HXY, HXY1, HX, HY and HXY2 are defined as:

$$HXY = -\sum_{i=1}^{N_g}\sum_{j=1}^{N_g} p(i,j)\log(p(i,j));$$

$$HXY1 = -\sum_{i=1}^{N_g}\sum_{j=1}^{N_g} p(i,j)\log\{p_x(i)p_y(j)\};$$

$$HXY2 = -\sum_{i=1}^{N_g}\sum_{j=1}^{N_g} p_x(i)p_y(j)\log\{p_x(i)p_y(j)\};$$

$$HX = -\sum_{i=1}^{N_g} p_x(i)\log\{p_x(i)\}; \text{ and}$$

$$HY = -\sum_{j=1}^{N_g} p_y(j)\log\{p_y(j)\},$$

wherein $p(i,j)$ is an $(i,j)$-th matrix element of the normalized GLCM, $N_g$ is a number of grey levels in pixels of the image, and wherein $p_x(i)$ and $p_y(j)$ are defined as:

$$p_x(i) = \sum_{j=1}^{N_g} p(i, j); \text{ and}$$

$$p_y(j) = \sum_{i=1}^{N_g} p(i, j).$$

5. The method of claim 4, wherein the GLCM records how many times a pixel of one intensity appears adjacent to another pixel of another intensity.

6. The method of claim 2, wherein the first values are calculated for each section by:
dividing the section into subsections;
calculating a respective value of a measure of the at least one of the sharpness or the contrast of at least a part of the section for each of the subsections; and
determining the first value for the section based on at least one of the values calculated for the subsections.

7. The method of claim 6, wherein the first value for the section is calculated as one of a mean of the values calculated for the subsections or a maximum of the values calculated for the subsections.

8. The method of claim 1, wherein the respective third value is calculated for each section by dividing one of the calculated first value and the calculated second value by the other of the calculated first value and the calculated second value.

9. The method of claim 1, wherein the quality score is determined based on comparisons of at least some of the calculated third values with respective predetermined thresholds.

10. The method of claim 9, wherein the quality score is determined by processes of:
(i) grouping the sections into groups such that each of the groups comprises a respective one or more of the sections;
(ii) assigning a respective predetermined threshold to each of the groups;
(iii) for at least some of the sections, comparing the third value calculated for the section with the predetermined threshold that has been assigned to the group to which the section belongs; and
(iv) determining the quality score based on the comparison in process (iii).

11. The method of claim 1, wherein the calculated third values vary among the sections with a distribution having a peak, and the quality score is determined by determining at least one of a value of the peak, a flatness of the distribution, a width of the distribution and rate of fall-off of the distribution.

12. The method of claim 1, wherein the regions covered by the plurality of sections of the acquired image form one of an array of strips or a two-dimensional array of blocks.

13. The method of claim 1, further comprising:
generating display control signals for controlling a display device to display a spatial variation profile indicative of the variation of the calculated third values among the sections.

14. A non-transitory storage medium storing computer program instructions which, when executed by a processor, cause the processor to execute a method of assessing image quality of an image produced by a scanning imaging system, the method comprising:
acquiring image data of an image produced by the scanning imaging system;
calculating, for each section of a plurality of sections of the image covering different regions of the image
a respective first value of a measure of at least one of a sharpness or a contrast of at least a part of the section, the measure being dependent on noise in the at least a part of the section,
a respective second value that provides a measure of noise in at least a part of the section, and
a respective third value indicative of an image quality of the section by combining the respective calculated first value with the respective calculated second value,
wherein, in the calculation of the respective third value for each of the plurality of sections of the image, the respective calculated first value and the respective calculated second value are combined in the combining such that the third values calculated for respective sections of the plurality of sections have a weaker dependency on the noise than the first values calculated for respective sections of the plurality of sections; and
determining a quality score that is indicative of an image quality of the image based on a variation of the calculated third values among the sections.

15. An apparatus for assessing image quality of an image produced by a scanning imaging system, the apparatus comprising:
an image acquisition module arranged to acquire image data of an image produced by the scanning imaging system; and
a calculation module arranged to calculate, for each section of a plurality of sections of the image covering different regions of the image
a respective first value of a measure of at least one of a sharpness or a contrast of at least a part of the section, the measure being dependent on noise in the at least a part of the section,
a respective second value that provides a measure of noise in at least a part of the section, and
a respective third value indicative of an image quality of the section by combining the respective calculated first value with the respective calculated second value,
wherein the calculation module is arranged to
combine the respective calculated first value and the respective calculated second value in the calculation of the respective third value for each of the plurality of sections of the image such that the third values calculated for respective sections of the plurality of sections have a weaker dependency on the noise than the first values calculated for respective sections of the plurality of sections, and
determine a quality score that is indicative of an image quality of the image based on a variation of the calculated third values among the sections.

16. The apparatus of claim 15, wherein the calculation module is arranged to calculate each of the second values by at least one of
processing the at least a part of the section using Immerkaer's method,
calculating a statistical measure of noise in the at least a part of the section, and
generating a normalized grey level co-occurrence matrix, GLCM, for the at least a part of the section and calculating, as the second value, a variance measure based on the normalized GLCM, wherein the variance measure is calculated using any one of:

$$f_4 = \sum_{i=1}^{N_g}\sum_{j=1}^{N_g}(i-\mu)^2 p(i,j);$$

$$f_7 = \sum_{i=2}^{2N_g}(i-f_8)^2 p_{x+y}(i); \text{ and}$$

$$f_{10} = \text{variance of } p_{x-y},$$

wherein p(i,j) is an (i,j)th matrix element in the normalized GLCM, $N_g$ is a number of grey levels in pixels of the image, μ is a mean of p(i,j), and $p_{x+y}$, $p_{x-y}$ and $f_8$ are defined, respectively, as:

$$p_{x+y}(k) = \sum_{\substack{i=1 \\ i+j=k}}^{N_g}\sum_{j=1}^{N_g} p(i,j), k=2,3,\ldots,2N_g;$$

$$p_{x-y}(k) = \sum_{\substack{i=1 \\ |i-j|=k}}^{N_g}\sum_{j=1}^{N_g} p(i,j), k=0,1,\ldots,N_g-1; \text{ and}$$

$$f_8 = -\sum_{i=2}^{2N_g} p_{x+y}(i)\log\{p_{x+y}(i)\}.$$

17. The apparatus of claim 15, wherein the calculation module is arranged to calculate the respective first value for each section using the following expression which defines an entropy of the at least a part of the section:

$$-\sum_{i=1}^{n} P(x_i)\log_2\{P(x_i)\},$$

wherein $P(x_i)$ denotes a fraction of pixels in the at least part of a section that have a pixel value of $x_i$, where $x_1$ to $x_n$ are n quantization levels into which pixel values of the image data are quantised.

18. The apparatus of claim 15, wherein the calculation module is arranged to calculate the respective first value of the measure of the at least one of the sharpness and the contrast of at least a part of the section for each section by:

generating a normalized grey level co-occurrence matrix, GLCM, for the at least a part of the section; and calculating, as the first value, a textural feature based on the normalized GLCM, wherein the textural feature is calculated using any one of the following:

$$M1 = \frac{HXY - HXY1}{\max\{HX, HY\}}; \text{ and}$$

$$M2 = (1 - e^{-2(HXY2-HXY)})^{\frac{1}{2}},$$

wherein HXY, HXY1, HX, HY and HXY2 are defined as:

$$HXY = -\sum_{i=1}^{N_g}\sum_{j=1}^{N_g} p(i,j)\log(p(i,j));$$

$$HXY1 = -\sum_{i=1}^{N_g}\sum_{j=1}^{N_g} p(i,j)\log\{p_x(i)p_y(j)\};$$

$$HXY2 = -\sum_{i=1}^{N_g}\sum_{j=1}^{N_g} p_x(i)p_y(j)\log\{p_x(i)p_y(j)\};$$

$$HX = -\sum_{i=1}^{N_g} p_x(i)\log\{p_x(i)\}; \text{ and}$$

$$HY = -\sum_{j=1}^{N_g} p_y(j)\log\{p_y(j)\},$$

wherein p(i,j) is the (i,j)-th matrix element of the normalized GLCM, $N_g$ is a number of grey levels in pixels of the image, and wherein $p_x(i)$ and $p_y(j)$ are defined as:

$$p_x(i) = \sum_{j=1}^{N_g} p(i,j); \text{ and}$$

$$p_y(j) = \sum_{i=1}^{N_g} p(i,j).$$

19. The apparatus of claim 15, wherein the calculation module is arranged to calculate the first values for each section by:

dividing the section into subsections;

calculating a respective value of a measure of the at least one of the sharpness or the contrast of at least a part of the section for each of the subsections; and determining the first value for the section based on at least one of the values calculated for the subsections.

20. The apparatus of claim 19, wherein the calculation module is arranged to calculate the first value for the section as a mean of the values calculated for the subsections or a maximum of the values calculated for the subsections.

\* \* \* \* \*